US008656759B2

(12) United States Patent
Hughes et al.

(10) Patent No.: US 8,656,759 B2
(45) Date of Patent: Feb. 25, 2014

(54) HANDHELD PENETRATING CONSISTOMETER (75) Inventors: William C. Hughes, Woodstock, IL (US); John D. Guy, Soddy Daisy, TN (US)

(73) Assignee: Innoquest, Inc., Woodstock, IL (US)

( * ) Notice: Subject to any disclaimer, the term of this patent is extended or adjusted under 35 U.S.C. 154(b) by 259 days.

(21) Appl. No.: 13/050,350

(22) Filed: Mar. 17, 2011

(65) Prior Publication Data

US 2011/0226044 A1 Sep. 22, 2011

Related U.S. Application Data (60) Provisional application No. 61/340,533, filed on Mar. 18, 2010.

(51) Int. Cl.
*G01N 3/40* (2006.01)
*G01N 3/54* (2006.01)
(52) U.S. Cl.
CPC ... *G01N 3/40* (2013.01); *G01N 3/54* (2013.01)
USPC ............................ 73/81; 73/78; 73/85; 73/87
(58) Field of Classification Search
USPC ................................................. 73/78–85, 87
See application file for complete search history.

(56) References Cited

U.S. PATENT DOCUMENTS

| | | | | | |
|---|---|---|---|---|---|
| 1,540,979 | A | * | 6/1925 | Bloom | 73/54.36 |
| 1,646,195 | A | * | 10/1927 | German | 73/81 |
| 2,009,314 | A | * | 7/1935 | Gogan | 73/83 |
| 2,119,699 | A | * | 6/1938 | Bloom | 73/54.11 |
| 2,347,082 | A | * | 4/1944 | Claus | 73/169 |
| 2,816,439 | A | * | 12/1957 | Hayes | 73/81 |
| 3,712,121 | A | * | 1/1973 | Fletcher et al. | 73/84 |
| 4,061,021 | A | * | 12/1977 | Baldwin et al. | 73/84 |
| 4,112,742 | A | * | 9/1978 | Zahn | 73/54.01 |
| 4,302,967 | A | * | 12/1981 | Dufey | 73/84 |
| 4,332,160 | A | * | 6/1982 | Baragar et al. | 73/84 |
| 4,480,481 | A | * | 11/1984 | Buchele | 73/784 |
| 4,492,111 | A | * | 1/1985 | Kirkland | 73/84 |

(Continued)

OTHER PUBLICATIONS

"Digital, Static Cone Penetrometer HS-4210", available on the Internet Archive at <http://web.archive.org/web/20080827180226/http://www.humboldtmfg.com/pdf/HS-4210.pdf> Aug. 27, 2008.*

(Continued)

*Primary Examiner* — David A Rogers
(74) *Attorney, Agent, or Firm* — Rienhart Boerner Van Deuren P.C.

(57) ABSTRACT

A portable handheld consistometer that includes a probe having a shaft and a probe tip attached to a first end of the shaft. In an embodiment, the probe tip has a cross-sectional area greater than that of the shaft, the probe configured to be inserted into a material to measure the consistency thereof. In an embodiment, a force sensor is attached to a second end of the shaft opposite the first end. The force sensor is coupled to processing circuitry, and is configured to measure the force with which the probe tip penetrates the material. In an embodiment, a distance sensor is coupled to the processing circuitry. The distance sensor is configured to measure the distance that the probe tip penetrates into the material. Further, the handheld consistometer includes a display screen coupled to the processing circuitry and configured to display the results of consistency measurements.

19 Claims, 5 Drawing Sheets

(56) References Cited

U.S. PATENT DOCUMENTS

| | | | |
|---|---|---|---|
| 4,499,906 A * | 2/1985 | Wohlgemuth et al. | 600/589 |
| 4,856,318 A * | 8/1989 | Hogan et al. | 73/12.13 |
| 5,224,469 A * | 7/1993 | Mocny | 601/108 |
| 5,313,825 A * | 5/1994 | Webster et al. | 73/81 |
| 5,483,821 A * | 1/1996 | Mazzoleni et al. | 73/82 |
| 5,726,349 A * | 3/1998 | Palmertree et al. | 73/84 |
| 5,798,940 A * | 8/1998 | Bratton et al. | 700/267 |
| 6,138,501 A * | 10/2000 | Rastegar | 73/82 |
| 6,643,599 B1 * | 11/2003 | Mohr et al. | 702/108 |
| 6,976,387 B2 * | 12/2005 | Anthe et al. | 73/83 |
| 6,983,643 B2 * | 1/2006 | Brighton et al. | 73/81 |
| 7,284,414 B2 * | 10/2007 | Wu | 73/79 |
| 7,299,686 B2 * | 11/2007 | Briaud et al. | 73/84 |
| 7,387,015 B2 * | 6/2008 | Chancellor et al. | 73/85 |
| 7,493,803 B2 * | 2/2009 | Kelleher et al. | 73/84 |
| 8,074,496 B2 * | 12/2011 | Brandestini | 73/79 |
| 2007/0277598 A1 * | 12/2007 | Zacny et al. | 73/84 |
| 2010/0071474 A1 * | 3/2010 | Zou et al. | 73/803 |
| 2010/0192680 A1 * | 8/2010 | Brandestini | 73/82 |
| 2012/0004848 A1 * | 1/2012 | Kinast et al. | 702/2 |

OTHER PUBLICATIONS

"DIK-5530 Digital Cone Penetrometer", Daiki Rika Kogyo Co., Ltd, 2009.*

Clardy et al., "A Shortening Consistometer", American Oil Chemists Society, Dec. 1952.*

Swift Consistometer, Origin: Based on Bloom Consistency Tester; known prior to Mar. 23, 2011; pp. 11 and 1-6, 7 pages total.

* cited by examiner

Section A-A
Fig. 3

DETAIL C
Fig. 4

HANDHELD PENETRATING CONSISTOMETER

CROSS-REFERENCE TO RELATED PATENT APPLICATIONS

This patent application claims the benefit of U.S. Provisional Patent Application No. 61/340,533, filed Mar. 18, 2010, the entire teachings and disclosure of which are incorporated herein by reference thereto.

FIELD OF THE INVENTION

This invention generally relates to instruments for measuring the consistency or viscosity of materials.

BACKGROUND OF THE INVENTION

Conventional practice for measuring the consistency or viscosity of a material requires taking a sample of the material. The sample is then analyzed in one of two ways. For one, the sample may be taken into a lab and tested on a bench top instrument to provide the measurement. Alternately, the sample is placed inside a portable instrument that provides a measurement by spreading or deforming the material across a calibrated plate. Bench top equipment may test the sample for consistency by penetrating the sample with a specially formed tip. Either the depth of penetration is measured after applying a set force or impact, or the force is measured that is required to probe into the material a set distance.

Conventional practice requires removal of the product to be tested from its original environment. Since the consistency of most products are temperature dependant this practice can result in erroneous readings even if tested on laboratory equipment since the temperature of the product may have changed during the testing or while being transported from one location to another.

It would therefore be desirable to have a portable apparatus which allows for testing of the product in its current location. This simplifies the number of steps required to test a product and hence the time required. It would also be desirable if the apparatus could allow measurements to be taken in the product's original environment without requiring a sample to be taken. It would further be desirable if the apparatus could be handheld with electronic sensors, display, and memory so that measurements could be saved and transferred to a computer for analysis and archiving.

Embodiments of the present invention provide such an apparatus. These and other advantages of the invention, as well as additional inventive features, will be apparent from the description of the invention provided herein.

BRIEF SUMMARY OF THE INVENTION

In one aspect, embodiments of the invention provides a handheld consistometer configured to measure a product's consistency by forcing a special tip into the product sample and measuring the insertion force. This insertion force or a derivative of the insertion force is provided as the consistency measurement of the product. The force of insertion is affected by several factors other than the physical properties of the product which are intended to be measured. First is the size and shape of the tip. It is therefore desirable to always use the same tip size and geometry when trying to make comparable readings. Second is the speed of insertion. Generally, a faster insertion speed will yield a higher insertion force in a given product than a slower insertion force. In a particular embodiment, the insertion speed is controlled via a non-contact distance sensor.

In another aspect, embodiments of the invention provide a specially shaped tip mounted on a shaft. The other end of this shaft is attached to a force sensor and electronic circuit to measure and display readings. In a particular embodiment, the electronic circuit is attached to a non-contact distance sensor that provides readings of the penetration depth into the product being measured. In a more particular embodiment, handles on the body of the handheld consistometer allow a user to hold the invention during use and apply force as necessary during a measurement. Embodiments of the invention further incorporate a temperature sensor near the specially shaped tip to allow the electronic circuit to measure and record the temperature of the product being tested at the depth of penetration.

In yet another aspect, embodiments of the invention provide a handheld consistometer configured to measure tip penetration force while monitoring penetration speed in real time. In a particular embodiment, the consistometer's display shows the user if the specially shaped tip is penetrating too fast or too slow, thus allowing the user to adjust the downward force to attain the correct penetration speed. Maintaining a consistent penetration speed provides repeatable results from reading to reading and from user to user.

In a particular embodiment, the handheld consistometer allows for the measurement of a material's consistency without requiring a sample to be removed. For example, this allows measurements to be taken on the material while inside mixing vats, storage containers, shipping containers, and on production lines.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Figure 1:
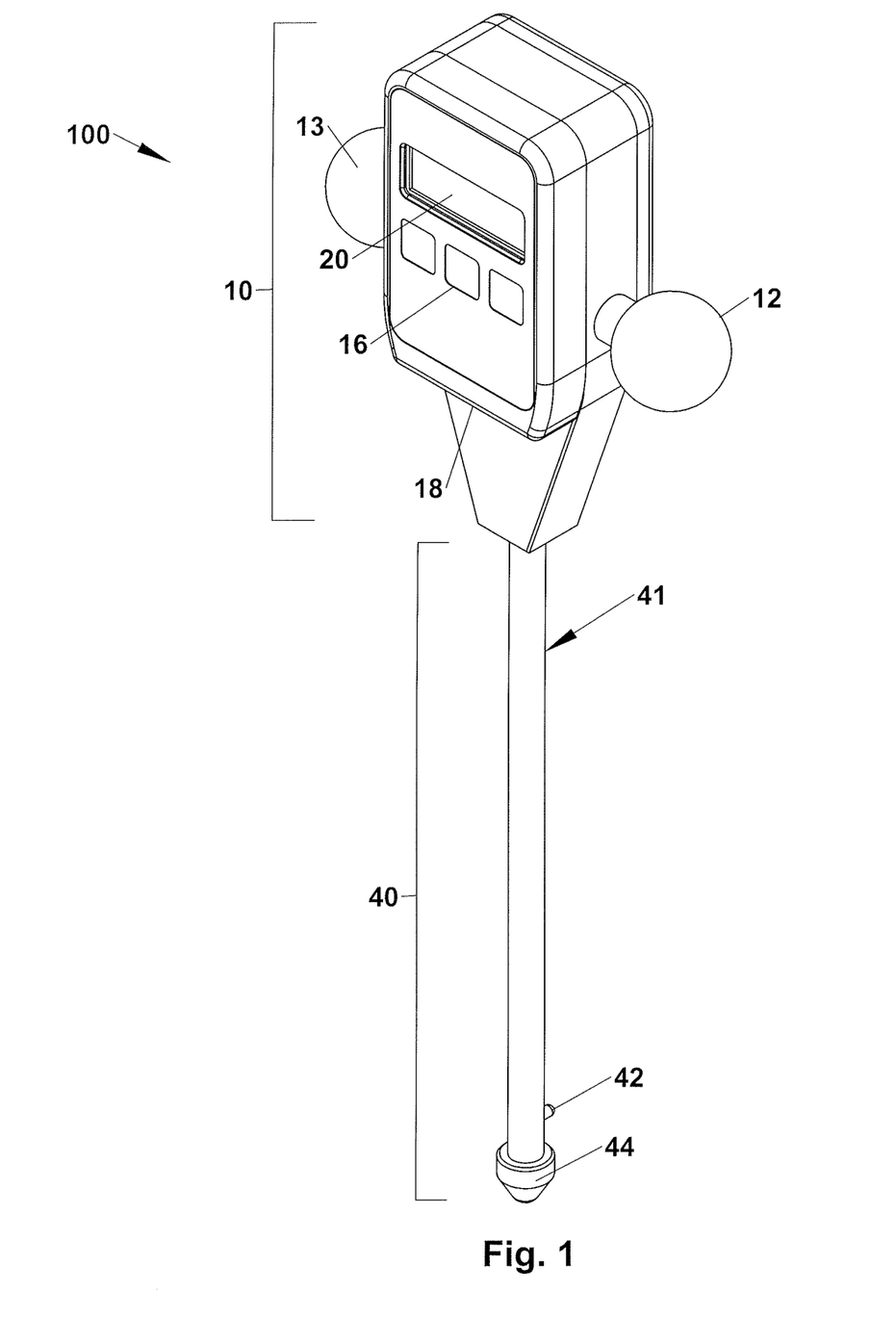
FIG. 1 is a perspective view of a handheld penetrating consistometer, constructed in accordance with an embodiment of the invention.
Figure 2:
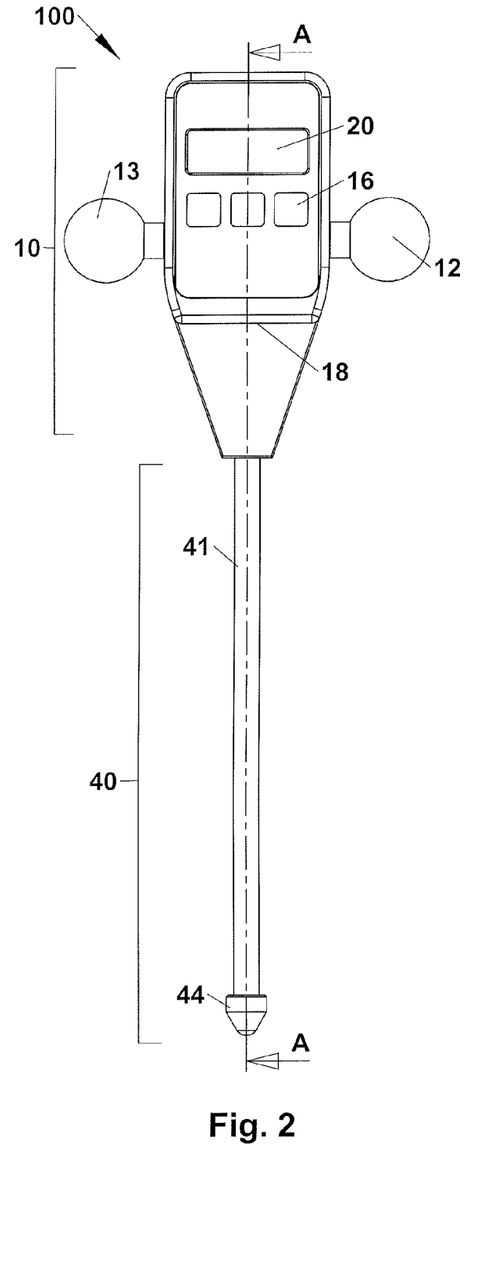
FIG. 2 is a front view of the penetrating consistometer of FIG. 1.
Figures 3, 4:
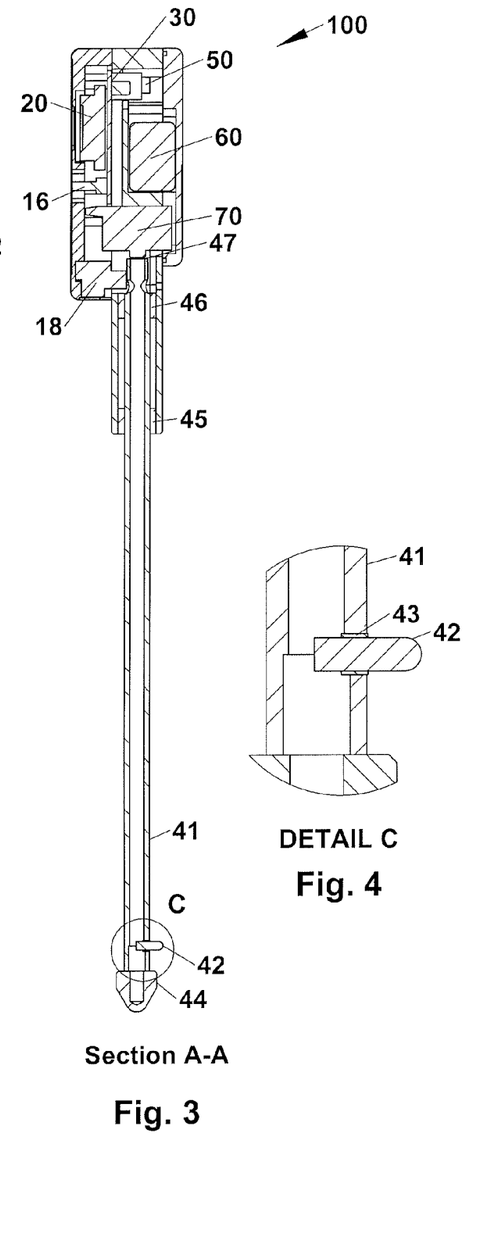
FIG. 3 is a cross-sectional view of the penetration consistometer of FIG. 1.
FIG. 4 is a close up detail view of the section view of FIG. 3.

A portable handheld consistometer 100, constructed in accordance with an embodiment of the invention, is shown in FIGS. 1-8. The handheld consistometer consists of a meter body 10 and a protruding probe 40, which includes a probe shaft 41, special tip 44, and may include temperature sensor 42. A display 20 and key pad 16 are built into meter body 10 such that they are easily visible and accessible to a user. An electronic circuit 80 is placed on circuit board 30 contained in meter body 10 and is powered by replaceable battery 60. Protruding probe 40 extends from meter body 10 such that one end of probe shaft 41 is attached to a force sensor 70. The other end of the probe shaft 41 is attached to special tip 44. In the embodiment of FIG. 3, the temperature sensor 42 is placed near an end of the probe shaft 41 for measuring the temperature of the material under test at the depth of probing.

A distance sensor 18 is disposed in meter body 10 such that its field of view and sensing are pointed in the direction of the protrusion of protruding probe 40 such that the distance sensor 18 will measure the distance from said sensor to the surface of the product being tested. In particular embodiments, the distance sensor 18 is a non-contact distance sensor 18, which provides certain advantages for the handheld consistometer 100, as will become apparent from the description below. In some of the embodiments described herein, distance sensor 18 is referred to as non-contact distance sensor 18. Due to the fixed geometry of protruding probe 40 relative to the meter body 10 and therefore to non-contact distance sensor 18, the depth of penetration can be calculated by the electronic circuit.

Handles 12 and 13 are attached to either side of probe body 10 so that a user can securely hold and manipulate the invention with both hands for maximum control while forcing protruding probe 40 into the product under test while viewing display 20 to adjust penetration speed. A portion 22 of display 20 is dedicated to real-time display of the relative penetration speed to allow a user to accurately maintain a constant preset speed. A data port 50 allows connection of electronic circuit 80 to a computer for transfer of data, and allows the settings on the handheld consistometer 100 to be changed as needed.

Referring now to FIG. 1 in more detail, the meter body 10 may be constructed of metal or non-metallic materials such that sufficient strength and ease of manufacture is available to support the pressure applied during the insertion process. In at least one embodiment, the handheld consistometer 100 has a meter body 10 constructed of both metal and plastic components. In a particular embodiment, the metal portion is made from anodized aluminum to provide corrosion resistance, strength, and to limit the weight of the device. In particular embodiments, the plastic portion is made from acetal which is easy to clean and strong enough to withstand damage from dropping.

In a further embodiment, the front of meter body 10 has a display 20 and keypad buttons 16 which are located as such so that they face the user when both hands are placed on handles 12, 13 during use. Positioning of the handles 12, 13 in this fashion gives the user good visibility of the protruding probe 40 entering the product and of the display 20 during use. This allows the user to quickly scan several aspects of operation without requiring movement of their head which could affect their ability to continue to steadily press the meter into the product under test. In at least one embodiment, a portion of the back side of meter body 10 may be removed to allow replacement of battery 60 when needed. Additionally, a removable plug is provided on the back side of meter body 10 for access to data port 50 when handheld consistometer 100 is connected to a computer for either configuration of settings or transfer of data to a computer.

It is contemplated that in particular embodiments, the probe shaft 41 is removable from the meter body 10. Removal of the probe shaft 41 from the meter body 10 allows for convenient storage or transport when not in use. The probe shaft 41 may be constructed of metal, plastic, or fiberglass. In at least one embodiment, the probe shaft 41 is made from stainless steel so that it may be corrosion resistant, strong, and easy to clean when used with food products, for example.

The length of protruding probe 40 is selected so that penetration may be made as deep as desired in the product under test, but still allowing meter body 10 to remain far enough above the product to remain clean and to position the display 20 to remain clearly visible to the user. The diameter or cross-sectional area of the probe shaft 41 is selected to be smaller than the outside diameter or cross-sectional area of special tip 44. Thus, as special tip 44 is forced into the product under test, clearance is made such that probe shaft 41 has limited drag against the material during the test, assuring that the force of insertion is generated primarily from the resistance of special tip 44.

Referring now to FIG. 2, special tip 44 is attached to the distal end of probe shaft 41. Special tip 44 may be attached to probe shaft 41 by welding, press fit, gluing, or threading. In particular embodiments of the handheld consistometer 100, this attachment is made by a threaded connection so that special tip 44 may be removed and replaced due to wear or the desire to install a tip with a different shape. The shape of special tip 44 may have a variety of different shapes, provided that the its outside diameter, or maximum cross-sectional area, is greater than that of the probe shaft 41. In at least one embodiment, the special tip 44 is stainless steel with a conical shape defined by a rounded nose. This geometry provides a self-centering action during insertion, further provides an insertion force that is in the measuring range of force sensor 70, and does not pose a hazard to the user as would a sharp point. It alternate embodiments of the invention, the special tip 44 is constructed of plastic, ceramic, or another suitable metal. For certain applications, stainless steel may be selected due to its chemical and physical durability, corrosion resistance, and ease of cleaning.

Referring to FIG. 3, the probe shaft 41 is supported from lateral movement by low friction bearings 45 and 46. These bearings allow axial movement of the probe shaft 41 so that axial forces, placed on the protruding probe 40 during insertion of special tip 44 into the material or product under test, are transmitted with minimal reduction to force sensor 70, to which upper end 47 of protruding probe 40 is attached. In this manner, the protruding probe 40 is attached to meter body 10 and may be manipulated as such by a user holding handles 12 and 13.

As stated above, the force sensor 70 is configured to measure the insertion force of special tip 44. Force sensor 70 may be composed of any electronic force sensor such as a bending beam with strain gauge, for example, or a piezoresistive load cell, or some other type of force sensor whose sensing range matches that of the expected insertion forces. In at least one embodiment of the handheld consistometer 100, the force sensor 70 is a piezoresistive load cell with built-in temperature compensation. In particular embodiments, force sensor 70 is connected to circuit board 30 to provide its signal to electronic circuit 80.

With reference to FIG. 3 and FIG. 4, temperature sensor 42 is described in more detail. Temperature sensor 42 is configured to sense the temperature of the product being tested by handheld consistometer 100. Temperature sensor 42 is located near the special tip 44 so that the sensing of temperature is near the location that the penetration resistance is being measured. Placement of the temperature sensor 42 near the special tip 44 improves the performance of the handheld consistometer 100 because the penetration resistance of many materials, especially food products, is dependant upon their temperature. Additionally, this allows for the measurement of temperatures deep within the product under test which generally provides better results than measurement of surface temperature, since a measurement of surface temperature would not likely be representative of the bulk product. Surface temperature is easily and quickly influenced by the outside environment and could lead to imprecise readings of the product's consistency. That said, there may be situations where it is desirable to employ a non-contact temperature sensor, such as an infrared (IR) sensor to take temperature readings of the material under test. In a particular embodiment, the IR temperature sensor is located in meter body 10 and takes temperature readings from the surface of the material or product under test. Because it does not come into contact with the product under test, the IR sensor would be relatively easy to maintain and keep clean.

Temperature sensor 42 may be constructed of plastic, glass, or metal. In a particular embodiment of the handheld consistometer 100, temperature sensor 42 is constructed of a stainless steel shell with a thermistor embedded in thermally conductive paste inside. In particular embodiments, the probe shaft 41 is hollow, as shown in FIG. 3, to accommodate the wires that connect the circuit board 30 and temperature sensor 42. In the embodiment of FIG. 3, temperature sensor 42 protrudes from probe shaft 41 by a distance such that it extends beyond the outside diameter of special tip 44 so as to enter into the product under test while protruding probe 40 is being inserted. The distance that temperature sensor 42 extends beyond probe shaft 41, is however, not greater than required to meet this requirement but also not to cause extra force of insertion which would result in insertion resistances that are not primarily a function of the size and geometry of special tip 44.

To further improve the response time and accuracy of the temperatures sensed by temperature sensor 42, it is mounted to probe shaft 41 with a non-metallic insulator bushing 43, which acts as a thermal insulator or barrier. In a particular embodiment of the handheld consistometer 100, the insulator bushing 43 is made from plastic and is press fit into probe shaft 41. Further, in a more particular embodiment, the temperature sensor 42 is press fit into insulator busing 43 so that there is no metal to metal contact between temperature sensor 42 and any other metal surface. Once assembled in this manner, the hollow center of probe shaft 41 is filled with epoxy in this area to further provide mechanical strength to the mounting of temperature sensor 42 without reducing the thermal isolation of the sensor 42 from the probe shaft 41.

Referring again to FIG. 2 and FIG. 3, non-contact distance sensor 18 is positioned within meter housing 10 such that its field of view is pointed in the direction of protruding probe 40 so that it will measure the distance from the surface of the product under test in the general area of where the special tip 44 penetrates said surface. Non-contact distance sensor 18 may be an ultrasonic sensor or an optical sensor, such as infrared or laser. In a particular embodiment, the handheld consistometer 100 uses an infrared non-contact distance sensor 18 due to its small field of view and sensitivity to small changes in distance. The distance sensor 18 is connected to electronic circuit 80 on circuit board 30. In a particular embodiment, the non-contact distance sensor 18 is placed within meter housing 10 behind a clear window to allow for unhampered operation while making it easy to clean.

In an alternate embodiment of the invention, an ultrasonic distance sensor 18 could be used. Typically, ultrasonic sensors provide a larger field of view, which in some instances could affect the accuracy of its measurements due to proximity of other objects near the point. Contact-type distance sensors of distance measuring can also be used with embodiments of the handheld consistometer. However, contact-type distance sensors should be rugged enough to withstand the contact and should also be easy to clean and maintain due to their inherent contact with the material or product under test. Since the distance from special tip 44 to the meter body 10 is fixed, and since the distance from the non-contact distance sensor 18 is fixed in relation to the meter housing, it is therefore apparent that the distance from the surface of the product under test can be directly related to the distance special tip 44 has penetrated the product. By making frequent measurements of the penetration depth with contact-type or non-contact distance sensor 18, the speed of penetration can be determined since the time between each successive measurement is known.

This method is employed in electronic circuit 80 to display the deviation between the preset desired penetration speed and the true penetration speed. During use, the user can view this display of speed deviation and makes changes in the actual speed of penetration to match, or closely approximate, the preset desired penetration speed. In this way, a relatively constant penetration speed can be maintained from test probing to test probing and from user to user to assure that penetration force readings are consistent even though the consistometer 100 is handheld.

Figure 6:
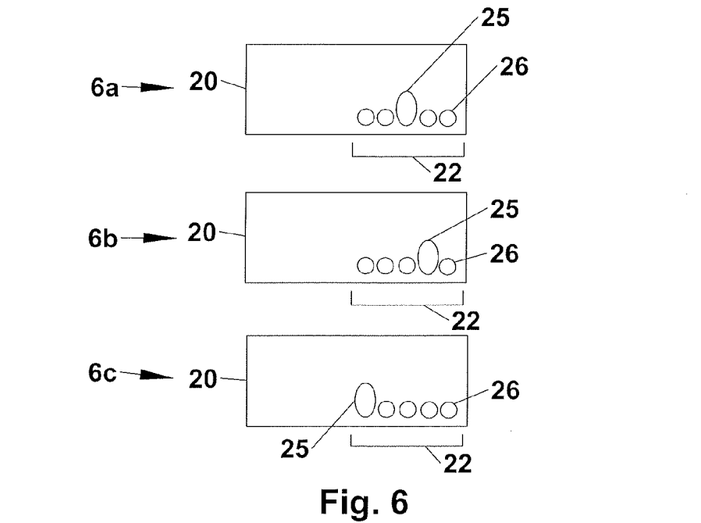
FIG. 6 is a drawing of the graphics used on the display of the penetrating consistometer of FIG. 1.

Referring now to FIG. 6, a portion 22 of display 20 is dedicated to showing the deviation in current penetration speed from that of the desired preset speed. The desired preset speed is set on the handheld consistometer 100 through the use of personal computer software that connects via the data port 50. The portion 22 of display 20 that shows the speed deviation is a series of small dots or "o"s 26 and a large dot or "O" 25. The relative position of large dot 25 in the row of small dots 26 provides a visual indication of the relation of the current speed of penetration to the desired speed. FIG. 6a shows how the portion 22 will look when the actual speed is equal to the desired speed. FIG. 6b shows how the portion 22 will look when the actual speed is slightly higher than the desired speed. FIG. 6c shows how the portion 22 will look when the actual speed is much slower than the desired speed.

In this way, there are a multitude of relative speed indications possible that can be easily communicated visually to a user so he or she may quickly change his or her actions during the penetration phase of a measurement. While any number of small dots 26 may be displayed, the handheld consistometer 100 uses 4 small dots 26 and one large dot 25 to indicate relative speed in this manner. This gives two levels of "too fast" and two levels of "too slow" indication in addition to the image which indicates relative speed is correct. It is understood that a greater number of small dots would add more resolution to the speed indication, however, the more visual information that is presented will also take longer for the user to interpret and act upon.

Figure 5:
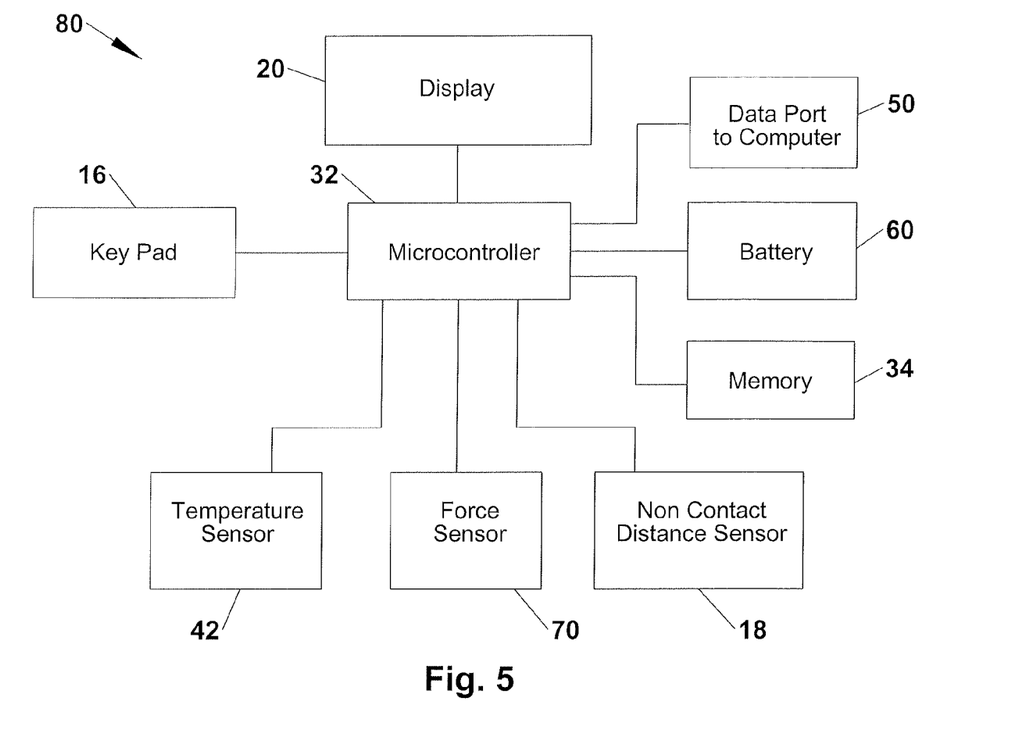
FIG. 5 is a block diagram of the electronic circuit of the penetrating consistometer of FIG. 1.

FIG. 5 is now described in detail. In the embodiment shown, electronic circuit 80 is mounted on circuit board 30 (shown in FIG. 3), which is contained in meter body 10. Electronic circuit 80 is comprised of a microcontroller 32 powered by replaceable battery 60. The user interface to microcontroller 32 is via keypad 16 and display 20. Keypad 16 is smooth on the outside surface on handheld consistometer 100 but may be of any type of button or membrane switch type. In an embodiment of the invention, display 20 is a liquid crystal display with backlight, but, in alternate embodiments, may be of other types such as LED. Temperature sensor 42, force sensor 70, and non-contact distance sensor 18 are all connected and send signals to microcontroller 32. In a particular embodiment, electronic circuit 80 contains non-volatile memory 34 which is connected to microcontroller 32 and serves to store settings and save data for handheld consistometer 100. Data port 50, which is connected to microcontroller 32, allows data and settings to be exchanged between a personal computer and handheld consistometer 100. In at least one embodiment, microcontroller 32 runs custom software code that handles all of the aforementioned sensors and peripherals and allows the handheld consistometer 100 to perform all necessary functions to act as a penetrating consistometer as described herewith.

Figure 7:
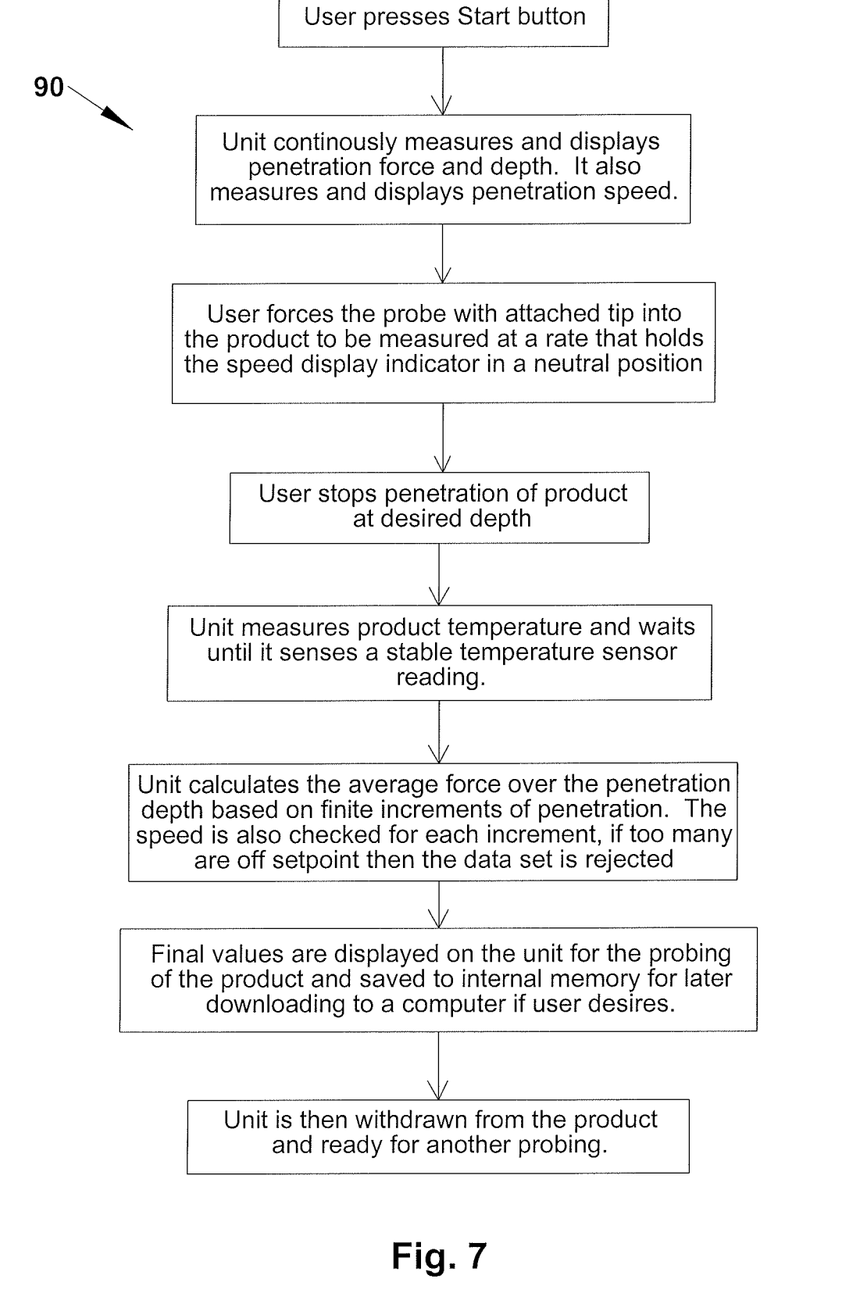
FIG. 7 is a flow chart of the operational sequence of the penetrating consistometer of FIG. 1.

Now referring to FIG. 7, the operation of the handheld consistometer 100 is described in the operation flow chart 90. As described, a reading of consistency is measured for a product and displayed on the display 20 of handheld consistometer 100 when the reading is complete. It should be noted that, in certain embodiments, the handheld consistometer 100 checks for stabilization of temperature via the temperature sensor 42 before notifying the user that the reading is complete. In a particular embodiment, this check is done by determining the rate of temperature change with microcontroller 32 and only allowing a final temperature to be reported once this rate of change is below a predetermined set point. In further embodiments, there is a detailed check of the recorded penetration speeds throughout set increments of the penetration depth to determine if a substantial portion of the probing depth failed to be at the correct penetration speed. The microcontroller 32 is configured to compare these recorded penetration speeds to preset limits. That is, if the number of recorded penetration speeds that fall outside of the preset limits exceeds a threshold value (e.g. a percentage value), the microcontroller determines that the resulting consistency measurement may be inaccurate. If so, then the user is notified via the display 20 that the reading is false, and no consistency measurement is displayed.

In a particular embodiment, once a test probing is completed, the handheld consistometer 100 saves the penetration force for each set increment of depth along with the average calculated over all but the first and last increments of depth. This is done to eliminate start-up and ending errors in the hand insertion process from the average value since they are most likely to have speed or force errors. In a more particular embodiment, the sensed equilibrated temperature of the product is also saved in memory 34. These saved values are all available for review on display 20 by pressing certain buttons on keypad 16. The saved values may also be transferred to a personal computer for other types of graphing, analysis, or archiving for quality control purposes via data port 50.

Figure 8:
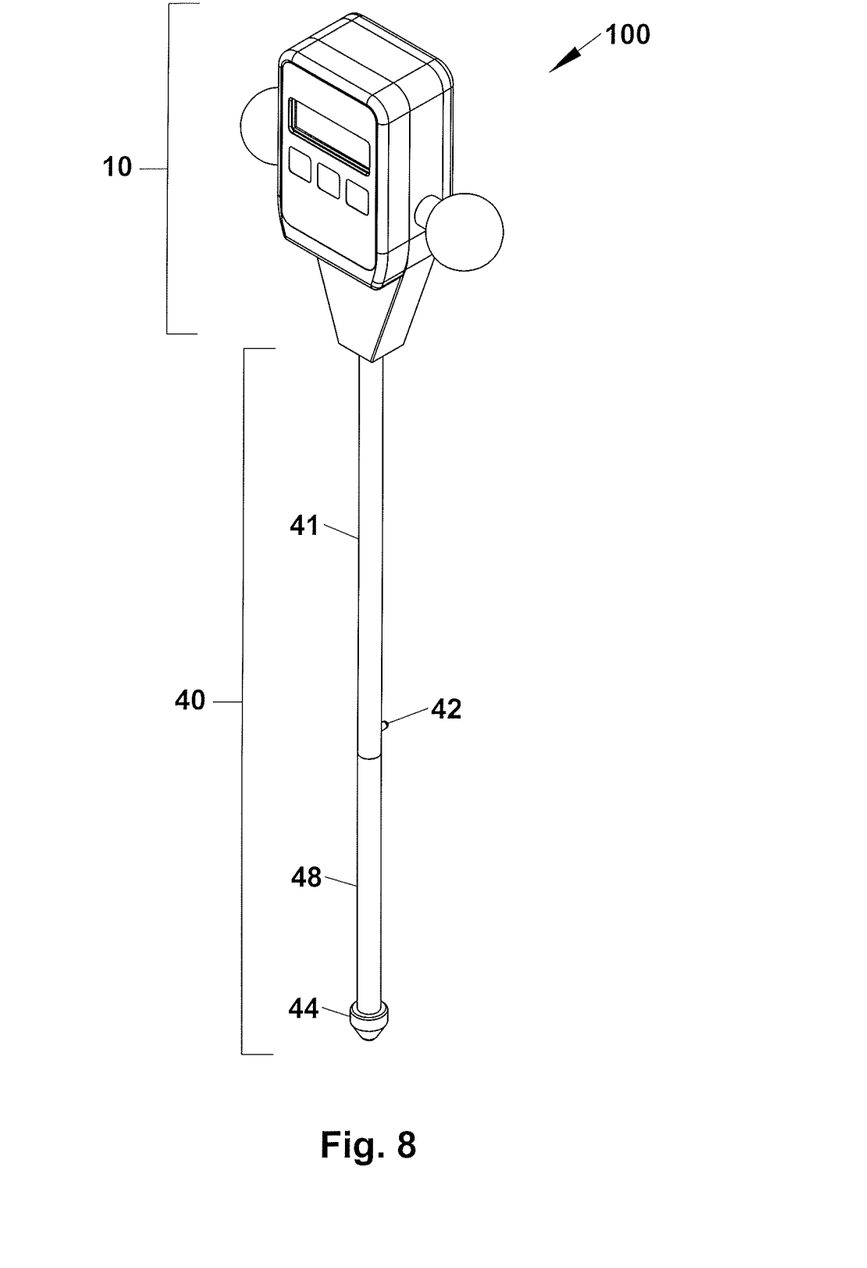
FIG. 8 is a perspective view of the handheld penetrating consistometer of FIG. 1 incorporating a shaft extension, according to an embodiment of the invention.

Now referring to FIG. 8, there is shown an embodiment of the handheld consistometer 100 with an optional probe shaft extension 48. In this manner, the protruding probe 40 may be extended in length by removing special tip 44 and adding the probe shaft extension 48 onto the probe shaft 41 and connecting the special tip 44 onto the end of the probe shaft extension 48. In this way, the handheld consistometer 100 may be configured to be used in products, packages, and containers of varying depths and sizes. Thus, in particular embodiments, it is advantageous to have the special tip 44 configured to be easily removed and attached to probe shaft 41 or to probe shaft extension 48. As such, the special tip 44 can be quickly removed from the probe shaft extension 48 and attached to probe shaft 41 when the probe shaft extension 48 is not being used.

As described herein, embodiments of the handheld consistometer 100 include the ability to transport the measuring probe to the product rather than having to take a sample of the product to the probe, which, in conventional consistometers, may be mounted on a fixed piece of laboratory equipment. Further, configuring the apparatus to be handheld provides flexibility with regard to where and how the meter is used. Further, the use of a sufficiently long shaft, or a shaft extension, allows for measurements throughout the whole depth of the product not just on the surface. This allows for a better representation of the bulk product consistency, which is desirable. Further, the use, in certain embodiments, of the non-contact distance sensor 18 to provide real time penetration speed feedback to the user while minimizing moving parts that can be difficult to clean is advantageous. Integral mounting of the temperature sensor 42 near the special tip 44 provides for the accurate measurement of product temperature at the point of consistency measurement. In particular embodiments, the automatic sensing of when the temperature sensor 42 has come into equilibrium before notifying the user to withdraw the probe from the product is also a feature of the invention. Further, in particular embodiments the handheld consistometer is configured to check the recorded penetration speeds through the whole penetration depth after a probing measurement is complete to determine how much of the probing was at the desired speed and then notify the user if a significant portion failed to meet the target speed.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein.

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A portable handheld consistometer comprising:
   a probe having a shaft and a probe tip attached to a first end of the shaft, the probe tip having a cross-sectional area greater than that of the shaft, the probe configured to be inserted into a material to measure the consistency thereof;
   a force sensor attached to a second end of the shaft opposite the first end, the force sensor also being coupled to processing circuitry, the force sensor configured to measure the force with which the probe tip penetrates the material;
   a distance sensor coupled to the processing circuitry, the distance sensor configured to measure the distance that the probe tip penetrates into the material; and
   a display screen coupled to the processing circuitry and configured to display the results of consistency measurements;
   wherein the microcontroller is configured to provide to the display an indication of the penetration speed of the probe tip into the material; and
   wherein the microcontroller is further configured to record a plurality of penetration speeds throughout set increments of the penetration depth, wherein if the number of recorded penetration speeds that fall outside of preset limits exceeds a threshold percentage value, no consistency measurement is displayed.

2. The portable handheld consistometer of claim 1, further comprising a temperature sensor positioned in the shaft adjacent to the probe tip.

3. The portable handheld consistometer of claim 1, wherein the force sensor comprises one of a piezoresistive load cell and a bending beam with a strain gauge.

4. The portable handheld consistometer of claim 1, further comprising a key pad configured to allow for user input.

5. The portable handheld consistometer of claim 1, further comprising a data port to allow for communication between the consistometer and a personal computer, such that device settings for the consistometer can be exchanged between the consistometer and personal computer.

6. The portable handheld consistometer of claim 1, wherein the microcontroller determines the penetration speed based on data provided by the distance sensor.

7. The portable handheld consistometer of claim 1, further comprising a shaft extension portion configured to attach to the shaft to extend the length thereof.

8. The portable handheld consistometer of claim 1, wherein the processing circuitry comprises a microcontroller.

9. The portable handheld consistometer of claim 8, wherein the microcontroller is powered by a battery.

10. The portable handheld consistometer of claim 1, wherein the distance sensor comprises a non-contact distance sensor.

11. The portable handheld consistometer of claim 10, wherein the distance sensor comprises one of an infrared-type distance sensor, a laser-type distance sensor, and an ultrasonic distance sensor.

12. A portable handheld consistometer comprising:
    a probe having a shaft and a probe tip attached to a first end of the shaft, the probe tip having cross-section area greater than that of the shaft, the probe configured to be inserted into a material to measure the consistency thereof;
    a force sensor attached to a second end of the shaft opposite the first end, the force sensor also being coupled to processing circuitry, the force sensor configured to measure the force with which the probe tip penetrates the material;
    a distance sensor coupled to the processing circuitry the distance sensor configured to measure the distance that the probe tip penetrates into the material:
    a display screen coupled to the processing circuitry and configured to display the results of consistency measurements; and
    a data port to allow for communication between the consistometer and a personal computer, such that device settings for the consistometer can be exchanged between the consistometer and personal computer;
    wherein data on desired preset speeds for various materials can be transferred from the personal computer to the consistometer.

13. A method of measuring the consistency of a material, the method comprising the steps of:
    attaching a probe to one or more sensors configured to measure parameter related to the consistency of the material, the one or more sensors being coupled to electronic circuitry capable of providing consistency measurements;
    using the probe tip of a portable handheld consistometer to penetrate the material;
    observing a display screen on the portable handheld consistometer to determine if the speed of penetration is within acceptable limits;
    adjusting the speed of penetration based on information provided on the display screen;
    obtaining the results from the consistency measurement provided on the display screen; and
    transferring a plurality of optimal penetration speeds from a computer o the portable handheld consistometer, which stores the plurality of optimal penetration speeds in memory.

14. The method of claim 13, further comprising observing the display screen on the portable handheld consistometer to determine if a recorded temperature is within acceptable limits.

15. The method of claim 13, wherein in attaching a probe to one or more sensors comprises attaching a probe shaft having an attached probe tip whose cross-sectional area is greater than that of the probe shaft.

16. The method of claim 13, wherein attaching a probe to one or more sensors comprises attaching a probe to a force sensor and to a distance sensor.

17. The method of claim 16 wherein obtaining the results from the consistency measurement comprises obtaining the results from the consistency measurement by coupling a microcontroller to the force and distance sensors, the microcontroller configured to interpret the readings from the force and distance sensor and to provide on the display screen consistency measurements based on those readings.

18. The method of claim 16, wherein attaching a probe to one or more sensors further comprises attaching the probe to a temperature sensor, the temperature sensor being located adjacent to the probe tip.

19. The method of claim 16, wherein attaching a probe to one or more sensors comprises:

attaching the probe to a force sensor comprising one of a bending beam with attached strain gauge and a piezoresistive load cell; and attaching the probe to a non-contact distance sensor comprising one of an infrared-type distance sensor, a laser-type distance sensor, and an ultrasonic distance sensor.

* * * * *

UNITED STATES PATENT AND TRADEMARK OFFICE
CERTIFICATE OF CORRECTION

| | |
|---|---|
| PATENT NO. | : 8,656,759 B2 |
| APPLICATION NO. | : 13/050350 |
| DATED | : February 25, 2014 |
| INVENTOR(S) | : William C. Hughes et al. |

It is certified that error appears in the above-identified patent and that said Letters Patent is hereby corrected as shown below:

In the Claims

In Column 10, Line 9, a --,-- should be inserted after --circuitry--

In Column 10, Line 41, the word "o" should be --to--

Signed and Sealed this
Twenty-seventh Day of May, 2014

Michelle K. Lee
*Deputy Director of the United States Patent and Trademark Office*